US011260034B2

(12) United States Patent
Chong et al.

(10) Patent No.: US 11,260,034 B2
(45) Date of Patent: Mar. 1, 2022

(54) METHOD OF USING NICLOSAMIDE DERIVATIVES

(71) Applicant: CHANG GUNG UNIVERSITY, Taoyuan (TW)

(72) Inventors: Kowit-Yu Chong, Taoyuan (TW); Ching-Ping Tseng, Taoyuan (TW)

(73) Assignee: CHANG GUNG UNIVERSITY, Taoyuan (TW)

(*) Notice: Subject to any disclaimer, the term of this patent is extended or adjusted under 35 U.S.C. 154(b) by 381 days.

(21) Appl. No.: 15/481,455

(22) Filed: Apr. 6, 2017

(65) Prior Publication Data

US 2018/0104199 A1   Apr. 19, 2018

(30) Foreign Application Priority Data

Oct. 14, 2016 (TW) ................. 105133255

(51) Int. Cl.
| | | |
|---|---|---|
| *A61K 31/167* | (2006.01) | |
| *A61K 38/01* | (2006.01) | |
| *A61K 31/122* | (2006.01) | |
| *A61K 38/39* | (2006.01) | |

(52) U.S. Cl.
CPC .......... *A61K 31/167* (2013.01); *A61K 31/122* (2013.01); *A61K 38/01* (2013.01); *A61K 38/39* (2013.01)

(58) Field of Classification Search
CPC .................................................. A61K 31/167
See application file for complete search history.

(56) References Cited

U.S. PATENT DOCUMENTS

| | | | | |
|---|---|---|---|---|
| 5,731,409 A | * | 3/1998 | Fields ................ | A61K 47/6435 530/300 |
| 2010/0035793 A1 | * | 2/2010 | Lim .................... | A61K 31/575 514/1.1 |
| 2013/0005802 A1 | * | 1/2013 | Chen .................. | A61K 31/00 514/521 |
| 2015/0361031 A1 | * | 12/2015 | Zhou .................. | C07D 265/30 514/44 R |

FOREIGN PATENT DOCUMENTS

| | | |
|---|---|---|
| KR | 10-2013-0026762 A | 3/2013 |
| WO | 2011/035321 A1 | 3/2011 |
| WO | 2012/143377 A1 | 10/2012 |
| WO | 2014/023329 A1 | 2/2014 |

OTHER PUBLICATIONS

Song et al. "A low-molecular-weight compound discovered through virtual screening inhibits Stat3 function in breast cancer cells", 2005, PNAS, vol. 102, No. 13, pp. 4700-4705 (Year: 2005).*

Kono et al. "Immunohistochemical detection of the lymphatic marker podoplanin in diverse types of human cancer cells using a novel antibody", 2007, International Journal of Oncology, vol. 31, pp. 501-508. (Year: 2007).*

Cho et al. CAS: 432179, 2012.*

Xiaomei Ren, Lei Duan, Qiang He, Zhang Zhang, Yi Zhou, Donghai Wu, Jingxuan Pan, Duanqing Pei, Ke Ding, "Identification of Niclosamide as a New Small-Molecule Inhibitor of the STAT3 Signaling Pathway", ACS Medicinal Chemistry Letters, Sep. 7, 2010, pp. 454-459, vol. 1, American Chemical Society.

Zhou Zhou, Francisca C. Gushiken, Doug Bolgiano, Brela J. Salsbery, Niloufar Aghakasiri, Naijie Jing, Xiaoping Wu, K. Vinod Vijayan, Rolando E. Rumbaut, Roberto Adachi, Jose A. Lopez, Jing-Fei Dong, "STAT3 Regulates Collagen-Induced Platelet Aggregation Independent of its Transcription Factor Activity", VA Author Manuscript, Jun. 19, 2015, pp. 1-22, U.S. Department of Veterans Affairs, U.S.

Zhenyu Li, M. Keegan Delaney, Kelly A. O'Brien, Xiaoping Du, "Signaling during Platelet Adhesion and Activation", NIH Public Access Author Manuscript, Dec. 2011, pp. 1-17, National Institutes of Health, U.S.

D. Ofori-Adjei; A. N. O. Dodoo; A. Appiah-Danquah; M. Couper, "A Review of the Safety Niclosamide, Pyrantel Triclabendazole and Oxamniquine", International Journal of Risk and Safety in Medicine, 2008, pp. 113-122, vol. 20, Issue No. 3, IOS Press, Switzerland.

C. Kent Kwoh, Alvan R. Feinstein, "Rates of Sensitivity Reactions to Aspirin: Problems in Interpreting the Data", Clinical Pharmacology and Therapeutics, Nov. 1986, pp. 494-505, vol. 40, Issue No. 5, Publisher: Elsevier B.V., U.S.A.

Liuqin Liang, Mingcheng Huang, Youjun Xiao, Shan Zen, Minxu Lao, Yaoyao Zou, Maohua Shi, Xiuyan Yang, Hanshi Xu, "Inhibitory Effects of Niclosamide on Inflammation and Migration of Fibroblast-Like Synoviocytes from Patients with Rheumatoid Arthritis", Inflammation Research, Feb. 24, 2015, pp. 225-233, vol. 64, Springer.

Zhou Zhou, Francisca C. Gushiken, Doug Bolgiano, Breia J. Salsbery, Niloufar Aghakasiri, Naijie Jing, Xiaoping Wu, K. Vinod Vijayan, Rolando E. Rumbaut, Roberto Adachi, Jose A. Lopez, Jing-Fei Dong, "Signal Transducer and Activator of Transcription 3 (STAT3) Regulates Collagen-Induced Platelet Aggregation Independently of its Transcription Factor Activity", Vascular Medicine, Jan. 29, 2013, pp. 476-485.

Xiaomei Ren, Lei Duan, Qiang He, Zhang Zhang, Yi Zhou, Donghai Wu, Jingxuan Pan, Duanqing Pei, Ke Ding, "Identification of Niclosamide as a New Small-Molecule Inhibitor of the STAT3 Signaling Pathway", Medicinal Chemistry Letters, Sep. 7, 2010, pp. 454-459, American Chemistry Society.

* cited by examiner

*Primary Examiner* — Rei Tsang Shiao (74) *Attorney, Agent, or Firm* — Cheng-Ju Chiang (57) ABSTRACT

Niclosamide derivatives are provided in the present invention. More particularly, the methods of using niclosamide derivatives for the manufacture of medicaments for suppressing platelet aggregation and preventing thrombosis-related diseases are provided. The niclosamide derivatives in the medicaments inhibit the production of thromboxane A2, therefore suppress platelet aggregation and prevent thrombosis-related diseases.

6 Claims, 7 Drawing Sheets

METHOD OF USING NICLOSAMIDE DERIVATIVES

TECHNICAL FIELD

At least one embodiment of the present invention provides the methods of using niclosamide derivatives. More particularly, at least one embodiment of the present invention provides the method of using niclosamide derivatives for the manufacture of a medication for suppressing platelet aggregation.

DESCRIPTION OF THE RELATED ART

2',5-dichloro-4'-nitrosalicylanilide, sold under the trade name niclosamide, has been widely accepted as treatments for taeniasis induced by Taeniasolium, Taeniasaginata, Diphyllobothriasislatum, or Hymenolepis nana infection. Niclosamide can be found in medications including Yomesan, Copharten, and Kontal for treating tapeworm or roundworm infections. The recommended therapy to treat taeniasis for adults is per os 2 g niclosamide as a single dose, repeated for 7 to 17 days. Niclosamide inhibits the oxidative phosphorylation in the mitochondria of intestinal tapeworms. By blocking the glucose uptake pathway, niclosamide shows a promising efficacy to remove tapeworms.

In an article published on The International Journal of Risk & Safety in Medicine in 2008, Alexander Nii Oto Dodoo reported niclosamide as "there is no information to suggest an unfavorable safety profile of the drug under current conditions of use" (International Journal of Risk & Safety in Medicine 20 (2008) 113-122). Some mild adverse events of niclosamide are documented, such as abdominal pain, fever, vomiting, fatigue and mild dizziness. However, none of these adverse events are associated with life-threatening risks. Niclosamide remains safe to use on adults, small children, and pregnant women. In recent years, niclosamide was identified as anti-cancer medications. Life & Brain GmbH, a German-based company, filed a patent application, WO2014023329, in WIPO and claimed the anti-cancer property of niclosamide. Similarly, The Max Delbrück Center for Molecular Medicine's patent application, WO2012143377, discloses the anti-metastasis property of niclosamide. However, no other indications are documented for niclosamide.

On the other hand, acetylsalicylic acid (2-(acetoxy)benzoic acid), sold under the trade name aspirin, is extensively used as a medication to treat pain, fever, and inflammation. Moreover, aspirin is identified as preventive medications for heart attack, stroke, blood clots, and some cardiovascular diseases. Based on aspirin's ability to suppress the thromboxane A2 synthesis, low-dose aspirin (baby aspirin) is seen as an effective medical intervention for platelet aggregation and myocardial infarction. However, according to an article published on Clinical Pharmacology & Therapeutics, aspirin induces severe adverse drug reactions in at least 0.3% to 0.9% of the overall population (ClinPharmacolTher. 1986 November; 40(5):494-505). For example, subjects with glucose-6-phosphate dehydrogenase deficiency or allergic to ibuprofen or naproxen are strongly forbidden to take aspirin to avoid allergic reactions and hemolytic anemia.

Accordingly, substitutes for the low-dose aspirin to prevent cardiovascular diseases are needed.

SUMMARY

At least one embodiment of the present invention provides a method of using niclosamide derivatives for the manufacture of a medication for inhibiting platelet aggregation. In the embodiment, niclosamide derivatives inhibit platelet aggregation at least by suppressing the synthesis of thromboxane A2.

At least one embodiment of the present invention provides a method of using niclosamide derivatives for the manufacture of a medication for preventing thrombosis-related diseases. In the embodiment, the thrombosis-related diseases comprise coronary artery embolism, stroke, pulmonary embolism, portal thrombosis, renal vein thrombosis, jugular vein thrombosis, inferior vena caval thrombosis, deep vein thrombosis, myocardial infarction, hepatic artery embolization, Budd-Chiari syndrome, Paget-Schroetter disease and the combination thereof.

At least one embodiment of the present invention provides a composition comprising a niclosamide derivative, collagen, and a pharmaceutically acceptable carrier. In the embodiment, collagen-induced human platelet activation will be interrupted by the niclosamide derivative comprised in the same composition. The composition may be formulated for injection. For example, the composition may be formulated as injectable fillers for subcutaneous injection or injection therapy for mitigating degenerative joint diseases.

At least one embodiment of the present invention provides a pharmaceutical composition comprising a niclosamide derivative, STA-21 (ochromycinone), and a pharmaceutically acceptable carrier. In the embodiment, the pharmaceutical composition can be used to suppress platelet agglutination.

At least one embodiment of the present invention provides medications for preventing cardiovascular diseases. Moreover, the medications are effective and safe for long-term use.

DESCRIPTION OF THE PREFERRED EMBODIMENTS

At least one embodiment of the present invention provides a method of using niclosamide derivatives. The niclosamide derivatives comprises niclosamide, modified niclosamide and the salts thereof. More particularly, the niclosamide derivatives have a general formula structure as below:

Wherein, R represents $NO_2$, Cl or $CF_3$.

In some embodiment, the niclosamide derivative is niclosamide (5-chloro-N-(2-chloro-4-nitrophenyl)-2-hydroxybenzamide) having a formula structure as below:

In some embodiment, the niclosamide derivative is BPR1H366 (55-chloro-N-(2,4-dichloro)-2-hydroxybenzamide) having a formula structure as below:

In some embodiment, the niclosamide derivative is BPR1H369 (5-chloro-N-(2-chloro-4-trifluoromethyl)-2-hydroxybenzamide) having a formula structure as below:

At least one embodiment of the present invention provides a method of using niclosamide derivatives for the manufacture of a medication for inhibiting platelet aggregation. In the embodiment, the niclosamide derivatives inhibit platelet aggregation at least by suppressing the synthesis of thromboxane A2.

At least one embodiment of the present invention provides a method of using niclosamide derivatives for the manufacture of a medication for preventing thrombosis-related diseases. In the embodiment, the thrombosis-related diseases comprise coronary artery embolism, stroke, pulmonary embolism, portal thrombosis, renal vein thrombosis, jugular vein thrombosis, inferior vena caval thrombosis, deep vein thrombosis, myocardial infarction, hepatic artery embolization, Budd-Chiari syndrome, Paget-Schroetter disease and the combination thereof. In some embodiment, the medication comprises an active ingredient and a pharmaceutically acceptable carrier, in which the active ingredient is a niclosamide derivative or a combination of niclosamide derivatives; in some preferred embodiments, the medication comprises an active ingredient, a STAT 3 inhibitor, and a pharmaceutically acceptable carrier, in which the active ingredient is one selected from the group consisting niclosamide, BPR1H366, and BPR1H369 and the combination thereof; in yet some preferred embodiment, the STAT 3 inhibitor is STA-21 (ochromycinone). In some embodiments, the medication is formulated to be administered orally; in some preferred embodiments, the medication is formulated to be administered daily to a subject. In some embodiments, the mechanism underlying the medication is to suppress the production of thromboxane A2.

At least one embodiment of the present invention is a composition comprising an active ingredient, collagen, and a pharmaceutically acceptable carrier, in which the active ingredient is a niclosamide derivative or a combination of niclosamide derivatives. In some embodiments, the composition comprises a niclosamide derivative, a STAT 3 inhibitor, collagen, and a pharmaceutically acceptable carrier; in one embodiment, the composition comprises an active ingredient, STA-21, collagen, and a pharmaceutically acceptable carrier, in which the active ingredient is one selected from the group consisting of niclosamide, BPR1H336, BPR1H339, and the combination thereof. In some embodiments, the composition is formulated for injection. For example, the composition may be stored in ampules or syringes, and formulated as injectable fillers for subcutaneous injection or injection therapy for mitigating degenerative joint diseases. In the embodiment, collagen-induced human platelet activation will be compromised by the niclosamide derivative comprised in the same composition.

At least one embodiment of the present invention is a pharmaceutical composition comprising an active ingredient, STAT 3 inhibitor, a pharmaceutically acceptable carrier, in which the active ingredient is a niclosamide derivative or a combination of niclosamide derivatives. In some embodiments, the pharmaceutical composition comprises an active ingredient, STA-21, and a pharmaceutically acceptable carrier, in which the active ingredient is one selected from the group consisting of niclosamide, BPR1H366, BPR1H369, and the combination thereof. In some preferred embodiments, the pharmaceutical composition is formulated to be administered orally; in yet some preferred embodiments, the pharmaceutical composition is formulated to be administered daily to a subject. In some embodiments, the pharmaceutical composition at least has the effect of inhibiting platelet aggregation.

Figure 1:
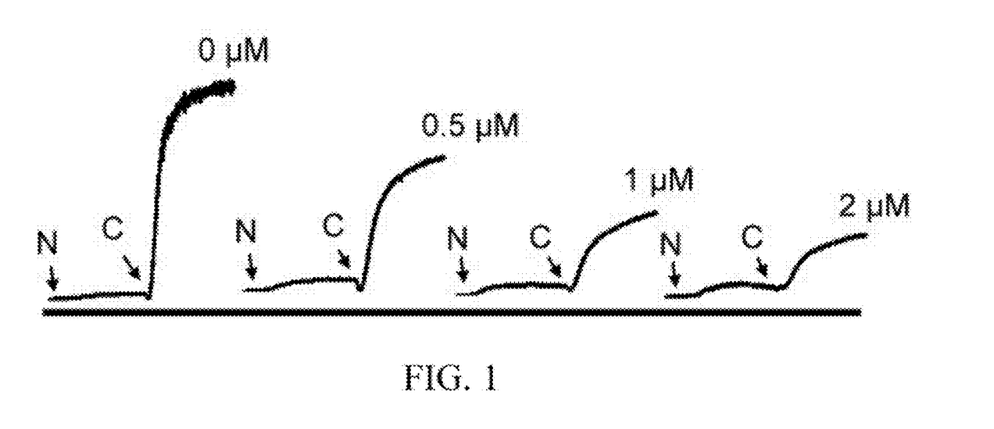
FIG. 1 is a diagram illustrating a platelet aggregation test, in accordance with at least one embodiment of the present invention.

FIG. 1 is a diagram illustrating a platelet aggregation test, in accordance with at least one embodiment of the present invention. In FIG. 1, N and C represent the administrations of niclosamide in 0.25% dimethyl sulfoxide (DMSO) or collagen respectively. The platelet aggregation test was performed in accordance with the standard procedure. Four washed platelet samples from the same source were treated with the same volume of niclosamide (0.5 µM, 1 µM, and 2 µM) or a solvent control respectively. Five minutes later, each washed platelet sample was treated with collagen (2 µM) to induce platelet aggregation. FIG. 1 illustrates the light transmission rates of each result. In FIG. 1, the X-axis represents time and the Y-axis represents the transmittance. Note that in FIG. 1, the four platelet aggregation tests performed simultaneously are presented sequentially on the X-axis to render the data readable for one skilled in the art.

According to the embodiment in FIG. 1, niclosamide suppresses the platelet aggregation induced by collagen in a dose-dependent manner. In this embodiment, the pretreatment of niclosamide inhibited platelet aggregation induced by the subsequent collagen administration.

Figure 2:
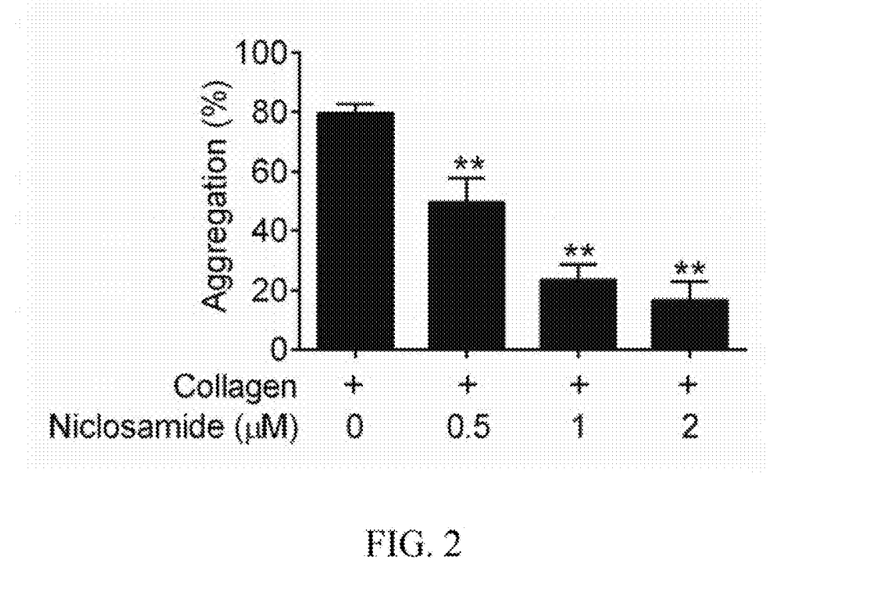
FIG. 2 is a bar chart representing the quantitative results of a platelet aggregation test, in accordance with at least one embodiment of the present invention.

FIG. 2 is a bar chart representing the quantitative results of a platelet aggregation test, in accordance with at least one embodiment of the present invention. The platelet aggregation test was performed in accordance with the standard procedure. Four washed platelet samples from the same source were treated with the same volume of niclosamide (0.5 µM, 1 µM, and 2 µM) or a solvent control respectively. Five minutes, each washed platelet sample was treated with 2 µM collagen to induce platelet aggregation. The results were detected twenty minutes after the administration of collagen. In FIG. 2, the Y-axis represents the percentage of platelet aggregation, in which the transmittance of platelet-poor plasma is set as 100%.

As illustrated in the embodiment of FIG. 2, niclosamide significantly suppresses the platelet aggregation induced by collagen. The percentages of platelet aggregation are significantly reduced (p<0.01) in the washed platelet samples received 0.5 µM, 1 µM or 2 µM niclosamide, as compared to the washed platelet sample received the solvent control (0 µM niclosamide). Moreover, niclosamide suppressed platelet aggregation in a dose-dependent manner. In this embodiment, the pretreatment of niclosamide inhibited platelet aggregation induced by the subsequent collagen administration.

Figure 3:
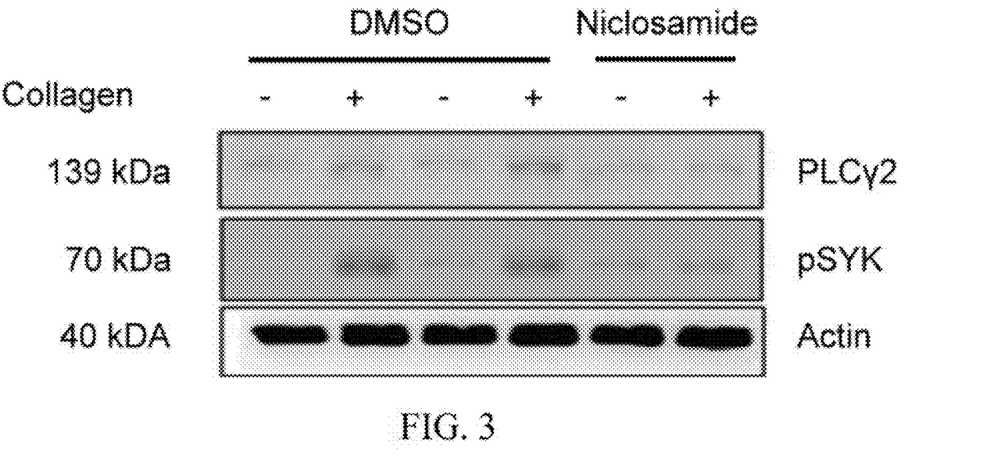
FIG. 3 is a western blot image showing proteins in the signal transduction pathway for platelet aggregation, in accordance with at least one embodiment of the present invention.

FIG. 3 is a western blot image showing proteins in the signal transduction pathway of platelet aggregation, in accordance with at least one embodiment of the present invention. In FIG. 3, pSYK and PLCγ2 in the signal transduction pathway are suppressed in the washed platelet sample received 2 µM niclosamide, even that is treated with 2.5 µM collagen to induce platelet aggregation. In contrast, the pSYK and PLCγ2 in the washed platelet sample received a solvent control (0.25% DMSO) pretreatment are successfully activated after the 2.5 µM collagen treatment. In this embodiment, the western blot image suggests that niclosamide pretreatment can suppress at least the pSYK and PLCγ2 in the signal transduction pathway.

Figure 4A:
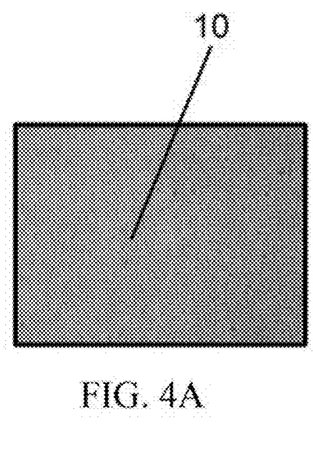
FIGS. 4A-4C are microscope images of a platelet aggregation test, in accordance with at least one embodiment of the present invention.
Figure 4B:
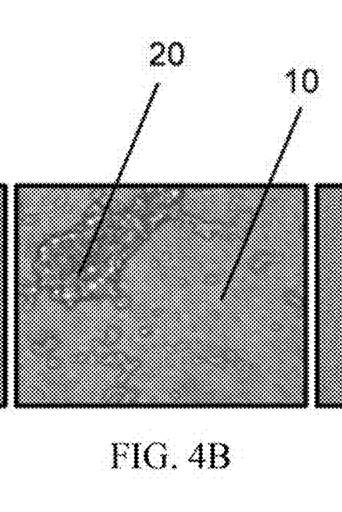
Figure 4C:
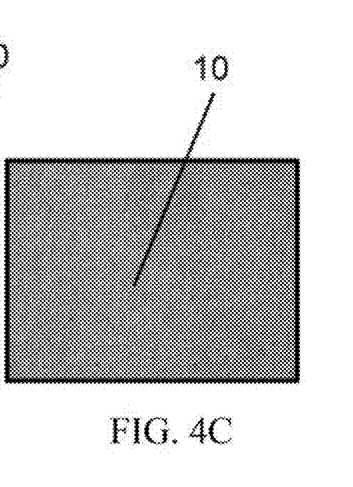

FIGS. 4A-4C are optical microscope images of a platelet aggregation test, in accordance with at least one embodiment of the present invention. The platelet aggregation test was performed in accordance with the standard procedure on three washed platelet samples from the same source at the same time. FIG. 4A shows a washed platelet sample 10 in its natural status without additional treatments. In FIG. 4C, the washed platelet sample 10 received 2 µM niclosamide and 2.5 µM collagen; In FIG. 4B, the washed platelet sample 10 received 2.5 µM collagen and 0.25% DMSO with the same volume of the niclosamide in FIG. 4C. Note that 0.25% DMSO is the solvent of the niclosamide in FIG. 4C. Under a 20× optical microscope, no platelet aggregation is observed in FIG. 4A as that the washed platelet sample was not induced by collagen. In FIG. 4B, clots 20 formed as a result of the treatment of collagen and DMSO. FIG. 4C, however, shows a pattern similar to FIG. 4A. No platelet aggregation is observed in FIG. 4C even after the treatment of collagen and niclosamide. In this embodiment, the optical microscope images suggest that niclosamide can prevent the platelet aggregation and clot formation induced by collagen.

Figure 5A:
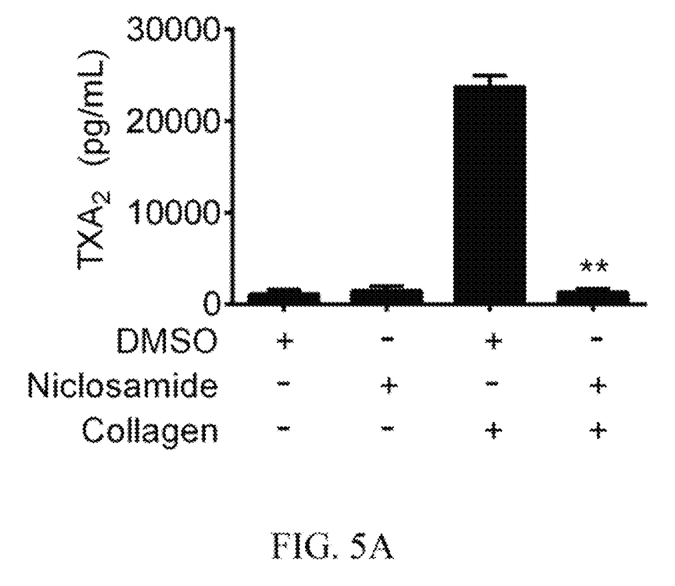
FIG. 5A is a bar chart representing the quantitative results of thromboxane A2, in accordance with at least one embodiment of the present invention.

FIG. 5A is a bar chart representing the quantitative results of thromboxane A2, in accordance with at least one embodiment of the present invention. The platelet aggregation test was performed in accordance with the standard procedure on four washed platelet samples from the same source at the same time. In FIG. 5A, "DMSO" represents 0.25% DMSO; "Niclosamide" represents niclosamide solved in 0.25% DMSO; and "Collagen" represents the stimulant, collagen. As indicated in FIG. 5A, the concentration of thromboxane A2 is significantly higher in the sample only treated with 2.5 µM collagen, as compared to the samples treated with neither DMSO or 2 µM niclosamide. However, the concentration of thromboxane A2 in the sample co-treated with 2.5 µM collagen and 2 µM niclosamide is similar to that of the sample not stimulated by collagen. The results in FIG. 5A and FIG. 3 are consistent. FIG. 5A and FIG. 3 suggest that niclosamide blocks the signal transduction pathway of platelet aggregation induced by collagen and thus decrease the concentration of the downstream product, thromboxane A2.

Figure 5B:
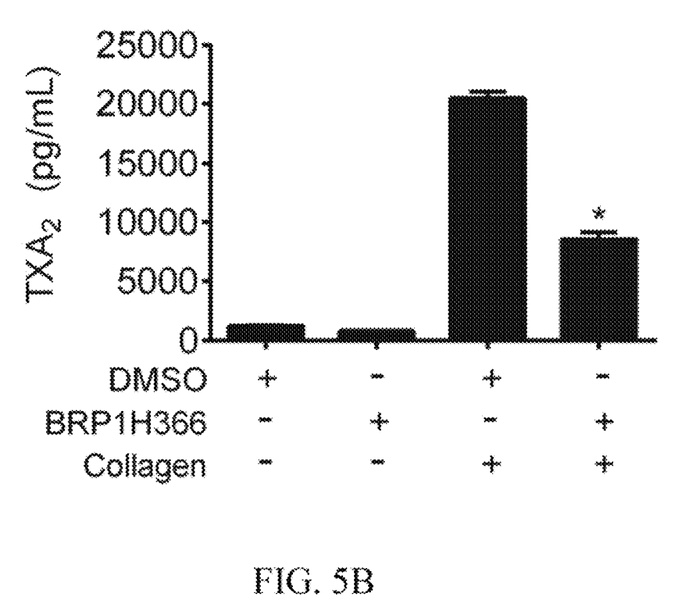
FIG. 5B is a bar chart representing the quantitative results of thromboxane A2, in accordance with at least one embodiment of the present invention.

FIG. 5B is a bar chart representing the quantitative results of thromboxane A2, in accordance with at least one embodiment of the present invention. The platelet aggregation test was performed in accordance with the standard procedure on four washed platelet samples from the same source at the same time. In FIG. 5B, "DMSO" represents 0.25% DMSO; "BPR1H366" represents BPR1H366 solved in 0.25% DMSO; and "Collagen" represents the stimulant, collagen. As shown in FIG. 5B, the concentration of thromboxane A2 is significantly higher in the sample only treated with 2.5 µM collagen, as compared to the samples treated with either DMSO or 2 µM BPR1H366. However, the concentration of thromboxane A2 in the sample co-treated with 2.5 µM collagen and 2 µM BPR1H366 is similar to that of the sample not stimulated by collagen. The results in FIG. 5B and FIG. 5A are highly similar. BPR1H366 also demonstrates the ability to suppress the concentration of thromboxane A2.

Figure 5C:
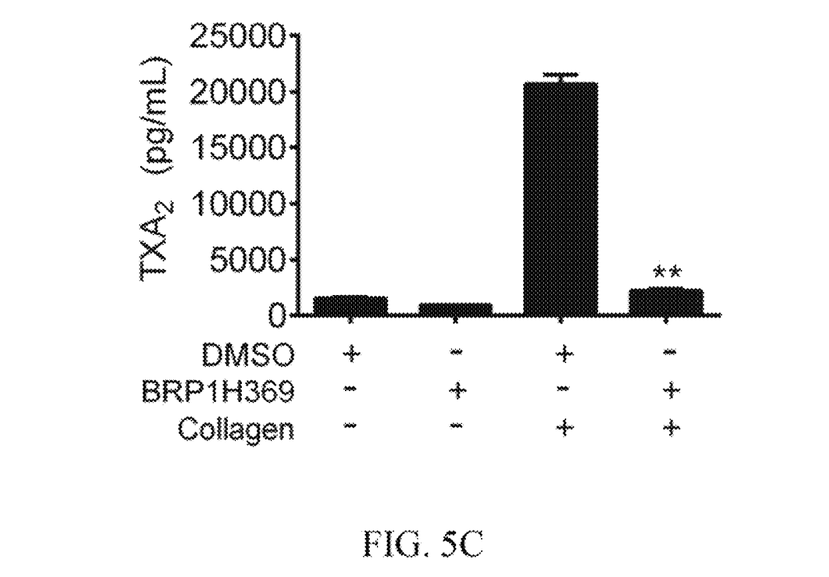
FIG. 5C is a bar chart representing the quantitative results of thromboxane A2, in accordance with at least one embodiment of the present invention.

FIG. 5C is a bar chart representing the quantitative results of thromboxane A2, in accordance with at least one embodiment of the present invention. The platelet aggregation test was performed in accordance with the standard procedure on four washed platelet samples from the same source at the same time. In FIG. 5B, "DMSO" represents 0.25% DMSO; "BPR1H369" represents BPR1H369 solved in 0.25%

DMSO; and "Collagen" represents the stimulant, collagen. As shown in FIG. 5C, the concentration of thromboxane A2 is significantly higher in the sample only treated with 2.5 μM collagen, as compared to the samples treated with either DMSO or 2 μM BPR1H369. However, the concentration of thromboxane A2 in the sample co-treated with 2.5 μM collagen and 2 μM BPR1H369 is similar to that of the sample not stimulated by collagen. The results in FIG. 5C and FIG. 5A are highly similar. BPR1H369 also demonstrates the ability to suppress the concentration of thromboxane A2.

Figure 6:
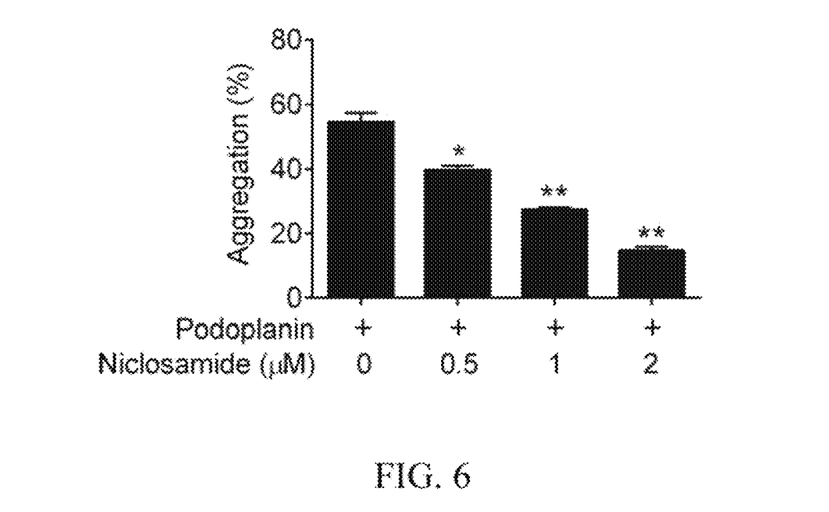
FIG. 6 is a bar chart representing the quantitative results of a platelet aggregation test, in accordance with at least one embodiment of the present invention.

FIG. 6 is a bar chart representing the quantitative results of a platelet aggregation test, in accordance with at least one embodiment of the present invention. All procedures in FIG. 6 are the same as the procedures in FIG. 2, except that the collagen used to stimulate platelet aggregation in FIG. 2 is substituted by podoplanin in FIG. 6. In this embodiment, four washed platelet samples from the same source were treated with the same volume of niclosamide (0.5 μM, 1 μM, and 2 μM) or a solvent control respectively. Five minutes, each washed platelet sample was treated with 0.4 μM podoplanin to induce platelet aggregation. The results were detected twenty minutes after the administration of podoplanin. In FIG. 6, the Y-axis represents the percentage of platelet aggregation, in which the transmittance of platelet-poor plasma is used as 100%.

As indicated by the embodiment of FIG. 6, niclosamide significantly suppressed the platelet aggregation induced by podoplanin. The percentages of platelet aggregation are significantly reduced in the washed platelet samples received 0.5 μM, 1 μM or 2 μM niclosamide, as compared to the washed platelet sample received the solvent control (0 μM niclosamide). Moreover, niclosamide suppressed platelet aggregation in a dose-dependent manner. In this embodiment, the pretreatment of niclosamide inhibits platelet aggregation induced by the subsequent podoplanin administration.

Figure 7:
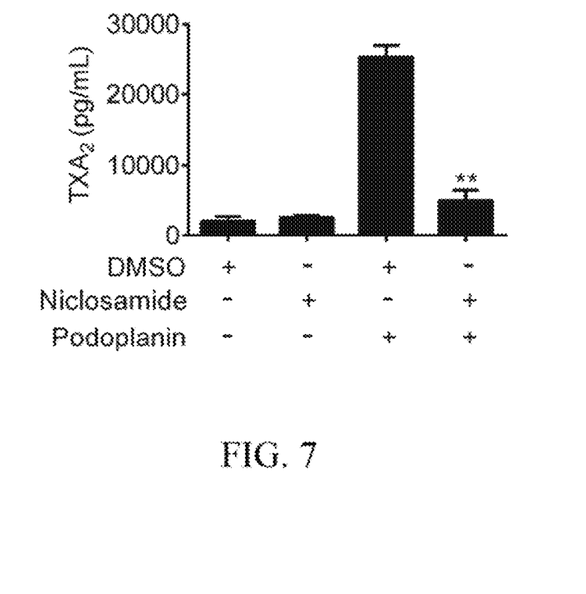
FIG. 7 is a bar chart representing the quantitative results of thromboxane A2, in accordance with at least one embodiment of the present invention.

FIG. 7 is a bar chart representing the quantitative results of thromboxane A2, in accordance with at least one embodiment of the present invention. The platelet aggregation test was performed in accordance with the standard procedure on four washed platelet samples from the same source at the same time. In FIG. 7, "DMSO" represents 0.25% DMSO; "Niclosamide" represents Niclosamide solved in 0.25% DMSO; and "Podoplanin" represents the stimulant, podoplanin. As indicated in FIG. 7, the concentration of thromboxane A2 is significantly higher in the sample only treated with 0.4 podoplanin, as compared to the samples treated with DMSO or 2 μM niclosamide. However, the concentration of thromboxane A2 in the sample co-treated with 0.4 μM podoplanin and 2 μM niclosamide is similar to that of the sample not stimulated by podoplanin. The results in FIG. 7 and FIG. 5A are highly similar. FIG. 7 shows that niclosamide significantly suppressed platelet aggregation and implies that niclosamide can suppress the signal transduction pathway of podoplanin and thus decrease the concentration of the downstream product, thromboxane A2.

Figure 8:
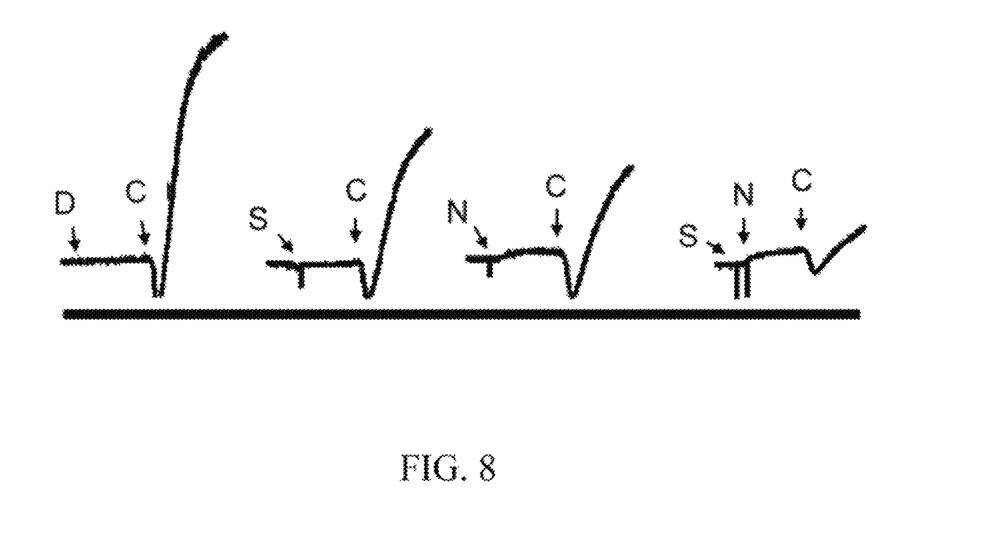
FIG. 8 is a diagram illustrating a platelet aggregation test, in accordance with at least one embodiment of the present invention.

FIG. 8 is a diagram illustrating a platelet aggregation test, in accordance with at least one embodiment of the present invention. Four washed platelet samples from the same source were treated with different treatments at the same time. In FIG. 8, "D" represents the administration of 0.25% DMSO; "C" represents the administration of collagen; "N" represents the administration of niclosamide in 0.25% DMSO; and "S" represents the administration of a STAT-3 inhibitor, STA-21. As shown in FIG. 8, the washed platelet sample only pretreated with DMSO aggregated immediately after received 2 μM collagen. However, the collagen-induced platelet aggregation of the washed platelet samples which are pretreated with 1.25 μM STA-21 or 0.25 μM was suppressed. Moreover, the synergistic effect of STA-21 and niclosamide on collagen-induced platelet aggregation is observed in the washed platelet sample co-treated with 1.25 μM STA-21 and 0.25 μM niclosamide. In FIG. 8, niclosamide shows a lower IC50 compared to STA-21. About 20% dosage of niclosamide can reach or even exceed the anti-coagulation effect of STA-21. Moreover, FIG. 8 implies that some mechanisms are not shared by niclosamide and STA-21, thus the co-treatment of niclosamide and STA-21 produces a synergistic effect.

Figure 9:
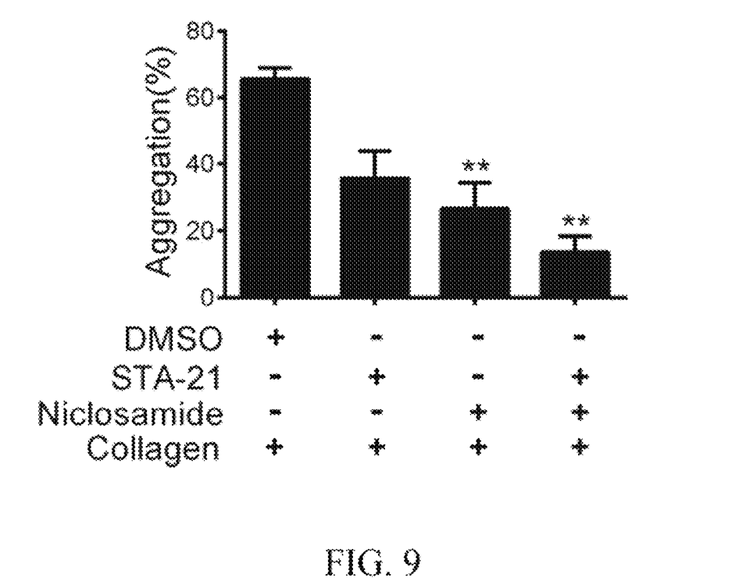
FIG. 9 is a bar chart representing the quantitative results of a platelet aggregation test, in accordance with at least one embodiment of the present invention.

FIG. 9 is a bar chart representing the quantitative results of a platelet aggregation test, in accordance with at least one embodiment of the present invention. Four washed platelet samples from the same source were treated with different treatments at the same time. In FIG. 9, "D" represents 0.25% DMSO; "STA-21" represents the STAT-3 inhibitor, STA-21; "Niclosamide" represents the niclosamide in 0.25% DMSO; and "Collagen" represents the stimulant, collagen. As shown in FIG. 9, the aggregation percentage exceeds 60% in the washed platelet sample treated with DMSO and 2 μM collagen. In contrast, the aggregation percentage is less than 40% in the sample treated with 1.25 μM STA-21 and 2 μM collagen, and the aggregation percentage is less than 30% in the sample treated with 0.25 μM niclosamide and 2 μM collagen. Moreover, the aggregation percentage dropped to around 15% in the sample treated with 2 μM collagen and both 1.25 μM STA-21 and 0.25 μM niclosamide. In FIG. 9, niclosamide shows a lower IC50 compared to STA-21. About 20% dosage of niclosamide can reach or even exceed the anticoagulation effect of STA-21. Moreover, FIG. 9 implies that some mechanisms are not shared by niclosamide and STA-21, thus the co-treatment of niclosamide and STA-21 produces a synergistic effect.

Figure 10:
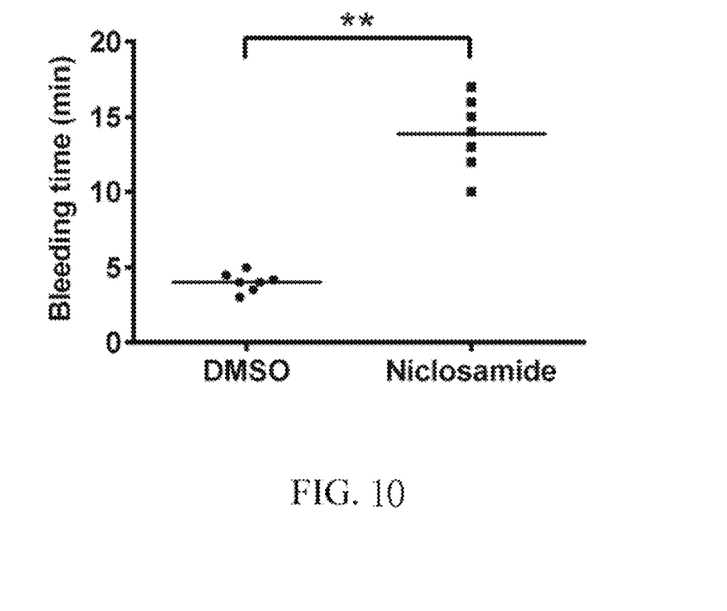
FIG. 10 is diagram illustrating the bleeding time, in accordance with at least one embodiment of the present invention.

FIG. 10 is diagram illustrating the bleeding time results, in accordance with at least one embodiment of the present invention. Mice at 8-10 weeks of age were used in FIG. 10. Isoflurane was provided based on the body weight to anesthetize the mice one hour after the 20 mg/kg niclosamide or 5% DMSO was injected into the abdomen. Followed the standard procedure of tail bleeding assay, the distal 3-mm segment of the tail was amputated with scalpel after the anesthetization. The tails were than immersed in isotonic saline at 37° C. to observe the bleeding time. As shown in FIG. 10, the bleeding of mice treated with DMSO ceased in 5 minutes. However, the bleeding time for mice treated with niclosamide was extended to around 15 minutes. FIG. 10 demonstrates that niclosamide inhibits platelet aggregation at both cell level and body level, as evidenced by the prolonged bleeding time observed in this tail bleeding assay.

Figure 11:
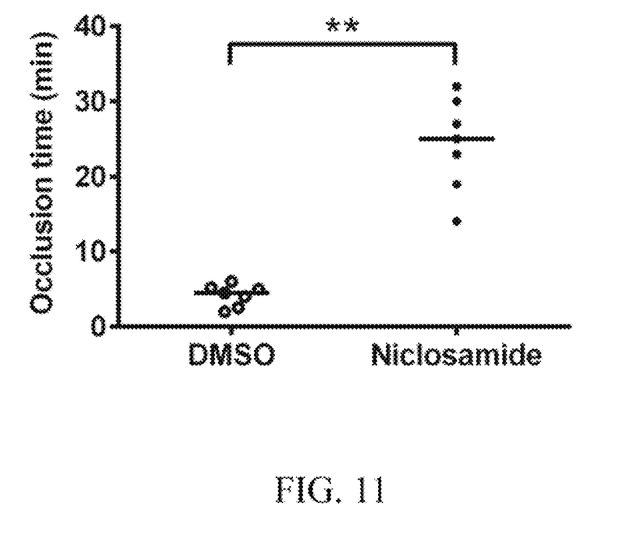
FIG. 11 is diagram illustrating the occlusion time, in accordance with at least one embodiment of the present invention.

FIG. 11 is diagram illustrating the occlusion time, in accordance with at least one embodiment of the present invention. Mice at 8-10 weeks of age were used in FIG. 11. About 20 nM 3,3'-Dihexyloxacarbocyanine iodide (DioC$_6$), a fluorescent dye used for the staining of platelets, was injected into the orbital vein after 20 mg/kg niclosamide or 5% DMSO was injected into the abdomen. An hour later, isoflurane was provided based on the body weight to anesthetize the mice. Followed the standard procedure for studying occlusive thrombosis, Whatman #1 filter papers soaked with 7.5% ferric chloride (FeCl$_3$) were attached to the mesenteric arteries for two minutes. The mesenteric arteries were then immersed in isotonic saline and placed under a fluorescence microscope (Macrofluo, objective 5.0/0.5 NA, Leica Micro-systems) to record the occlusion time and cessation of blood flow. As shown in FIG. 11, the occlusion occurred in 5 minutes for mice treated with DMSO, but extended to around 25 minutes for mice treated with niclosamide. FIG. 11 demonstrates that niclosamide inhibits platelet aggregation at both cell level and body level, as evidenced by the prolonged occlusion time.

In some embodiments, 2-2000 mg/kg niclosamide is recommended for IV injection. In some preferred embodiments, 5-2000 mg/kg niclosamide is recommended. In yet some preferred embodiments, 10-1500 mg/kg is recommended. In yet again some preferred embodiments, 10-1000 mg/kg is recommended.

There are many inventions described and illustrated above. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

What is claimed is:

1. A method of treating a patient having podoplanin or collagen induced thrombosis-related diseases by a medication for inhibiting platelet aggregation, comprising the step of concurrently administering to the patient an amount of niclosamide or its derivative, podoplanin or collagen and a pharmaceutically acceptable carrier to treat said thrombosis-related diseases;

wherein the niclosamide or its derivative have a general formula structure as below:

wherein, R is $NO_2$, Cl or $CF_3$;

wherein the thrombosis-related diseases comprise coronary artery embolism, hepatic artery embolization, mesenteric arterial thrombosis or the combination thereof.

2. The method as claimed in claim 1, wherein the medication further comprises STA-21(ochromycinone).

3. The method as claimed in claim 2, wherein the medication is formulated to be administered orally.

4. The method as claimed in claim 3, wherein the medication is formulated to be administered daily to a subject.

5. The method as claimed in claim 1, wherein the medication is a substitute for treating the patient who has severe adverse drug reaction induced by acetylsalicylic acid (2-(acetoxy)benzoic acid, Aspirin);

wherein the severe adverse drug reaction is allergic reactions or hemolytic anemia.

6. The method as claimed in claim 5, wherein the medication further comprises STA-21(ochromycinone).

* * * * *